United States Patent [19]
Dell'Acqua et al.

[11] 3,961,048
[45] June 1, 1976

[54] WATER-SOLUBILIZED ANTIBIOTICS

[75] Inventors: Ernani Dell'Acqua; Rodolfo Ferrari, both of Milan, Italy

[73] Assignee: SPA-Societa prodotti Antibiotici S.p.A., Milan, Italy

[22] Filed: May 14, 1974

[21] Appl. No.: 469,889

[30] Foreign Application Priority Data
May 14, 1973 United Kingdom............... 22848/73

[52] U.S. Cl. ............................................. 424/122
[51] Int. Cl.² ........................................ A61K 35/74
[58] Field of Search ................................... 424/122

[56] References Cited
UNITED STATES PATENTS

| | | | |
|---|---|---|---|
| 3,773,925 | 11/1973 | Bruzzese et al. | 424/122 |
| 3,780,173 | 12/1973 | Bruzzese et al. | 424/122 |

*Primary Examiner*—Jerome D. Goldberg
*Attorney, Agent, or Firm*—Wenderoth, Lind & Ponack

[57] ABSTRACT

The present invention provides a water-soluble pharmaceutical composition, comprising partricin and/or partricin methyl ester in admixture with at least one anionic and/or cationic surfactant.

3 Claims, No Drawings

WATER-SOLUBILIZED ANTIBIOTICS

BACKGROUND OF THE INVENTION

In our U.S. Pat. Nos. 3,773,925 and 3,780,173, we have described and claimed a new antibiotic, which we have called partricin, and its methyl ester.

Partricin is a polyenic antibiotic and, more precisely, is a heptaenic substance which can be obtained by fermentation of a new strain of *Streptomyces aureofaciens*, filed at the United States Department of Agriculture, Agricultural Research Services, Northern Utilisation Research and Development Division, Peoria (USA), which has been assigned the number NRRL 3878. This antibiotic exhibits a marked antifungal activity, particularly against certain pathogenic strains of *Candida albicans*, and also has a marked anti-protozoal activity, especially against *Trichomonas vaginalis*.

The partricin methyl ester is obtained by treating a solution of partricin in an appropriate organic solvent with a slight excess of diazomethane, in order to prevent the possible formation of products with higher degrees of reaction, and then leaving the reaction mixture to stand for a few hours (or at least until the evolution of nitrogen has ceased, this being proof that the reaction has taken place). The reaction product is then precipitated by adding an appropriate solvent. This semi-synthetic antibiotic, partricin methyl ester, also exhibits a marked antifungal activity, especially against certain pathogenic strains of *Candida albicans* and against protozoa, i.e. *Trichomonas*. It also has the advantage over the parent antibiotic, partricin, of having a reduced degree of toxicity.

Both these antibiotics are, however, practically insoluble in water; in our above-mentioned United States Patent Specifications, in relation to the toxocological properties of partricin and methyl partricin, we mentioned their therapeutic use for many human and animal diseases caused by fungi and protozoa. We described the use of these antibiotics by topical application in the form of ointments, liniments or creams for dermatological purposes, or in the form of inserts or suppositories (effervescent or ordinary) for endovaginal use against mycoses and protozoal infections. Furthermore, because of their low solubility in water, we indicated, for general use, the administration thereof by the oral route only for combating mycotic or protozoal intestinal infections: since these antibiotics are not absorbed, they can only exert their activity in the intestines.

Literature, however, amply describes infections of a generalised mycotic or protozoal type (for example pulmonary mycosis) in which, obviously, administration by the topical route would be ineffective.

The two new polyenic antibiotics have a good solubility in dimethyl sulphoxide, dimethyl acetamide and pyridine (i.e. in solvents not used in the therapeutic field for parenteral administration), whereas they are practically insoluble in water and in the common organic solvents. As we have already mentioned, their insolubility in water constitutes a marked limitation.

Therefore, it is an object of the present invention to render partricin and partricin methyl ester water-soluble so as to permit administration thereof by the parenteral or oral route and to guarantee blood antibiotic levels which are high enough to combat generalised mycotic or protozoal infections. Furthermore, this water-solubilisation is to be obtained without impairing the anti-fungal and antiprotozoal activity of partricin and methyl partricin.

During our researches we have found that certain anionic and cationic surfactants, for example the non-toxic salts of sulphated aliphatic hydrocarbons, such as sodium lauryl sulphate and sodium tetradecyl sulphate, as well as benzalkonium chlorides and the like are able to make partricin, as well as partricin methyl ester, soluble in water. Of all the surfactants which we have tested, sodium lauryl sulphate shows the best water-solubilising properties.

SUMMARY OF THE INVENTION

Thus, according to the present invention, there is provided a water-soluble pharmaceutical composition, comprising partricin and/or partricin methyl ester in admixture with at least one anionic and/or cationic surfactant.

DETAILED DESCRIPTION OF THE INVENTION

The solubility in water of partricin and the partricin methyl ester in the presence of the surfactant depends upon the physical form of the antibiotic, maximum solubility being obtained when the active substance is in an amorphous form. This is obtained by dissolving the antibiotic in dimethyl sulphoxide and precipitating it with water or, in the case of partricin, by dissolving it in a 1:1 mixture of water and acetone at pH 11 obtained by adding triethylamine and precipitating the partricin by lowering the pH to about 5 by adding hydrochloric acid.

The solubility in water of partricin increases with the increase of the concentration of sodium lauryl sulphate, up to a maximum concentration of surfactant of 3%.

In the case of partricin methyl ester, too, the higher is the concentration of the surfactant, the higher is the solubility in water, up to a maximum concentration of 4% of sodium lauryl sulphate.

Since the solubility in water of the two antibiotics does not increase proportion-wise with the concentration in surfactant, the antibiotic/surfactant weight ratio which gives hydrosoluble compounds with the highest microbiological activity is preferably about 1 to 10, more preferably about 1 to 5 and most preferably about 1 to 2.

The antibiotic/surfactant complexes thus solubilised can be isolated from their aqueous solution by lyophilisation or by precipitation with, for example, sodium chloride. The complexes thus obtained are very soluble in water and in dimethyl sulphoxide but are practically insoluble in acetone, ether and lower alcohols.

It is interesting to note that the ultra-violet spectra of the solutions in dimethyl sulphoxide and ethanol of the hydrosoluble compounds have the same behaviour as those of the starting partricin and methyl ester thereof in the same solvents, whereas the ultra-violet spectra of the aqueous solutions of the hydrosoluble products have a much different behaviour.

The aqueous solutions of the antibiotic/surfactant complexes are physically stable.

Solutions of methyl partricin/sodium lauryl sulphate at concentrations of 2000 γ/ml activity kept at +4°C. for 24 hours, do not show any loss of microbiological activity, while the solutions of partricin/sodium lauryl sulphate are microbiologically less stable.

The following Examples are given for the purpose of illustrating the present invention:

EXAMPLE 1

3 g. crystalline partricin methyl ester (1 mg = 1000 Units) are dissolved in 60 ml. dimethyl sulphoxide; after stirring for 10 minutes, the solution is poured into 360 ml. water, containing 0.5% by weight sodium chloride, to precipitate the partricin methyl ester.

The amorphous precipitate thus obtained is filtered on a porous filter $G_4$ and washed with water; the wet product is then suspended in 30 ml. water and added to 270 ml. water containing 6 g. sodium lauryl sulphate.

After stirring for about 1 hour, solution is complete. The dissolved product can be isolated:
 a. by lyophilisation, or
 b. by adding to the solution 10% by weight sodium chloride.

The precipitate obtained is filtered and dried, thus yielding 8.8 g. of product which is soluble in water and has an activity of 320 Units/mg.

EXAMPLE 2

5 g. crystalline partricin (1 mg = 1000 Units) are dissolved in 100 ml. dimethyl sulphoxide. The resulting solution is poured into 600 ml. of a 0.5% by weight aqueous solution of sodium chloride to precipitate the partricin which is filtered off and washed with water. The precipitate is suspended in 50 ml. water and added to 450 ml. water containing 10 g. sodium lauryl sulphate.

The suspension is stirred for about one hour until solution is complete. The product can be obtained in a solid form by:
 a. lyophilisation, or
 b. adding to the solution 75 g. sodium chloride, filtering and drying the precipitate in a vacuum at 40°C.

Yield: 14.6 g. of hydrosoluble product with an activity of 280 Units/mg.

EXAMPLE 3

2 g. Partricin are dissolved in 40 ml. dimethyl sulphoxide; the solution is slowly poured into 240 ml. water, containing 0.5% by weight of sodium chloride to precipitate the partricin. The amorphous precipitate thereby obtained is filtered off, washed with water and resuspended in 20 ml. water. The suspension obtained is poured into 180 ml. water containing 6 g. sodium tetradecyl sulphate. After stirring for 1 hour, the product is filtered and lyophilised.

EXAMPLE 4

3 g. Methyl partricin are dissolved in 60 ml. dimethyl sulphoxide; the solution is slowly poured into 360 ml. water, containing 0.5% by weight sodium chloride to precipitate the methyl partricin. An amorphous precipitation is obtained, which is filtered off and suspended in 30 ml. water. The fine suspension obtained is added to 270 ml. water containing 9 g. sodium tetradecyl sulphate. After stirring for one hour, it is filtered and lyophilised.

EXAMPLE 5

1 g. Partricin is dissolved in 20 ml. dimethyl sulphoxide. The solution is poured into 120 ml. water containing 0.5% by weight sodium chloride. The amorphous precipitate is filtered off, washed with water and suspended in 10 ml. water. The suspension is added to 100 ml. water containing 4 g. 50% benzalkonium chloride. After stirring for one hour, it is filtered and lyophilised.

EXAMPLE 6

Example 5 is repeated but using the methyl ester of partricin.

EXAMPLE 7

4 g. Partricin are suspended in 240 ml. acetone/water (1:1). Triethylamine is added to adjust the pH to 11 and the mixture then stirred for 30 minutes. After filtration, the filtrate is adjusted cautiously and with external cooling to pH 5 by adding concentrated hydrochloric acid. The amorphous precipitate obtained is filtered off, washed with water and suspended in 40 ml. water. The suspension is poured into 350 ml. water containing 8 g. sodium lauryl sulphate. After stirring for one hour, it is filtered and lyophilised or is precipitated with sodium chloride.

The present invention also provides pharmaceutical compositions, which can be administered orally or parenterally, which additionally contain a solid or liquid pharmaceutical carrier.

Solid compositions for oral, rectal or vaginal administration include compressed tablets, effervescent tablets, pills, dispersible powders, capsules, granules and suppositories. In such solid compositions, the active material complex is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents and sweetening and flavouring agents.

The compositions according to the present invention, for oral administration, include capsules of absorbable material, such as gelatine, containing the active material, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The percentage of active complex in the compositions of the present invention may be varied, it being necessary that it should constitute a proportion such that a suitable dosage for the desired therapeutic effect shall be obtained. In the case of dosage units for oral administration, each unit can contain up to 2 g. of partricin or up to 3 g. of partricin methyl ester. In the case of compositions for topical, vaginal or rectal administration, the content of complex can be up to about 0.06% by weight.

Examples of pharmaceutical compositions containing the polyene antibiotic include the following:

EXAMPLE 8

Ointment
Composition:

| | |
|---|---|
| the product of Example 1 | 0.5 g. |
| alcoholic fats | 60 g. |
| lanolin | 15 g. |
| polyethylene glycol 1540 monostearate | ad 100 g. |

EXAMPLE 9

Liniment
Composition:

| | |
|---|---|
| the product of Example 3 | 0.5 g. |
| dimethylacetamide | 5 g. |
| anhydrous lanolin | 15 g. |
| cetyl alcohol | 30 g. |
| oleyl alcohol | 15 g. |
| sorbitan trioleate | 10 g. |
| polyethylene glycol 1540 monostearate | 24 g. |

EXAMPLE 10

Vaginal suppositories
Each vaginal suppository contains:

| | |
|---|---|
| the product of Example 7 | 5 mg. |
| dimethyl acetamide | 50 mg. |
| polyethylene glycol 1540 monostearate | 1.35 g. |
| cetyl alcohol | 0.500 g. |

EXAMPLE 11

Vaginal suppositories
Each vaginal suppository contains:

| | |
|---|---|
| the product of Example 1 | 25 mg. |
| dimethyl acetamide | 50 mg. |
| polyethylene glycol 1540 monostearate | 1.35 g. |
| cetyl alcohol | 0.500 g. |

The pharmaceutical compositions illustrated in Examples 8 to 11 above show valuable anti-fungal and anti-protozoal activity when administered to humans.

We claim:

1. A water-soluble pharmaceutical complex obtained by dissolving an antibiotic selected from the group consisting of partricin and partricin methyl ester in an aqueous solution containing a surfactant selected from the group consisting of benzalkonium chloride, sodium lauryl sulphate and sodium tetradecyl sulphate wherein the weight ratio of the antibiotic to the surfactant is 1 to 10, stirring the mixture thus-obtained to form a complex and isolating the complex by lyophilisation or precipitation.

2. A complex according to claim 1, wherein the weight ratio of antibiotic to surfactant is about 1 to 5.

3. A complex according to claim 1, wherein the weight ratio of antibiotic to surfactant is about 1 to 2.

* * * * *